United States Patent
McNicholas et al.

(10) Patent No.: US 6,733,507 B2
(45) Date of Patent: May 11, 2004

(54) INTRAOCULAR LENS INSERTION APPARATUS

(75) Inventors: Thomas M. McNicholas, Laguna Niguel, CA (US); Douglas J. Mastel, Rapid City, SD (US); Joel D. Anderson, Rapid City, SD (US); Renee J. Deskin, Mission Viejo, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 182 days.

(21) Appl. No.: 10/121,314

(22) Filed: Apr. 12, 2002

(65) Prior Publication Data

US 2003/0195522 A1 Oct. 16, 2003

(51) Int. Cl.$^7$ .............................. A61F 9/00; A61F 2/16
(52) U.S. Cl. ....................................... 606/107; 623/6.12
(58) Field of Search ........................ 606/107; 623/6.11, 623/6.12, 6.18

(56) References Cited

U.S. PATENT DOCUMENTS

| | | | |
|---|---|---|---|
| 4,573,998 A | 3/1986 | Mazzocco | |
| 4,681,102 A | 7/1987 | Bartell | |
| 4,747,404 A | 5/1988 | Jampel et al. | |
| 4,834,094 A | 5/1989 | Patton et al. | |
| 4,836,201 A | 6/1989 | Patton et al. | |
| 4,919,130 A | 4/1990 | Stoy et al. | |
| 5,007,913 A | 4/1991 | Dulebohn et al. | |
| 5,190,552 A | 3/1993 | Kelman | |
| 5,275,604 A | 1/1994 | Rheinish et al. | |
| 5,474,562 A * | 12/1995 | Orchowski et al. | 606/107 |
| 5,494,484 A | 2/1996 | Feingold | |
| 5,499,987 A | 3/1996 | Feingold | |
| 5,616,148 A | 4/1997 | Eagles et al. | |
| 5,620,450 A | 4/1997 | Eagles et al. | |
| 5,643,276 A * | 7/1997 | Zaleski | 606/107 |
| 5,653,715 A | 8/1997 | Reich et al. | |
| 5,653,753 A | 8/1997 | Brady et al. | |
| 5,735,858 A | 4/1998 | Makker et al. | |
| 5,800,442 A | 9/1998 | Wolf et al. | |
| 5,803,925 A * | 9/1998 | Yang et al. | 606/107 |
| 5,942,277 A | 8/1999 | Makker et al. | |
| 5,947,975 A * | 9/1999 | Kikuchi et al. | 606/107 |
| 6,002,982 A | 12/1999 | Fry | |
| 6,010,510 A | 1/2000 | Brown et al. | |
| 6,083,230 A | 7/2000 | Makker et al. | |
| 6,241,737 B1 * | 6/2001 | Feingold | 606/107 |
| 6,254,607 B1 * | 7/2001 | Makker et al. | 606/107 |
| 6,447,520 B1 * | 9/2002 | Ott et al. | 606/107 |
| 2003/0176870 A1 * | 9/2003 | Ott | 606/107 |

FOREIGN PATENT DOCUMENTS

| | | |
|---|---|---|
| WO | 9629956 | 10/1996 |
| WO | 9815244 | 4/1998 |

* cited by examiner

*Primary Examiner*—Pedro Philogene
*Assistant Examiner*—David A Bonderer
(74) *Attorney, Agent, or Firm*—Peter Jon Gluck

(57) ABSTRACT

An intraocular lens (IOL) insertion apparatus for implanting acrylic IOLs through smaller incisions. The insertion apparatus includes an insertion cartridge that receives the IOL and cooperates with a handpiece. The cartridge includes a longitudinal lumen from a loading chamber to an open distal mouth that gradually narrows in dimension so as to fold the acrylic IOL to a dimension of less than about 2.0 mm. The cartridge is made of a polymer, such as polypropylene, that includes a lubricity enhancing component concentrated at surfaces by a blooming process. A push rod in the handpiece enters the loading chamber of the cartridge and urges the IOL therethrough. A distal tip of the push rod has an irregular shape, such as a rounded trapezoidal, and has a maximum dimension slightly less than the inner diameter of the open distal mouth of the cartridge. The distal tip of the push rod may have a relief channel on one side that accommodates a trailing haptic of the IOL.

23 Claims, 4 Drawing Sheets

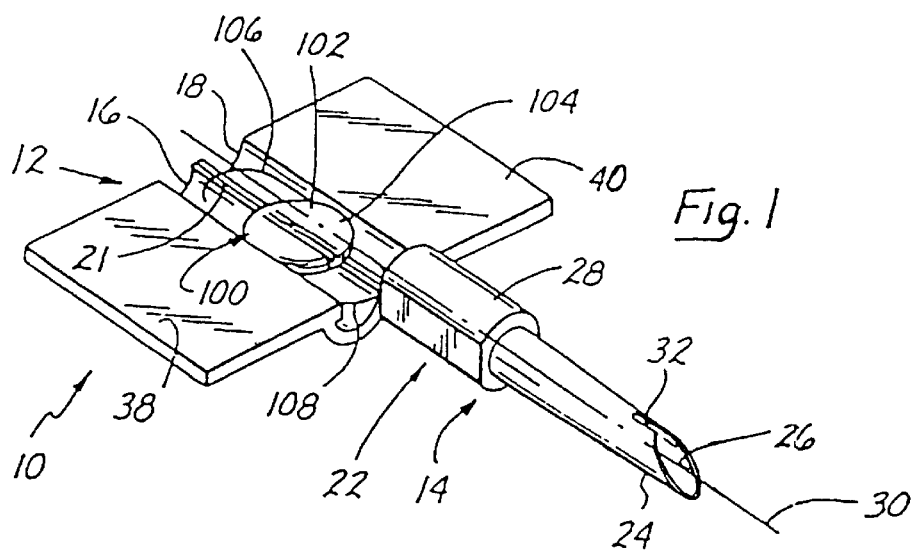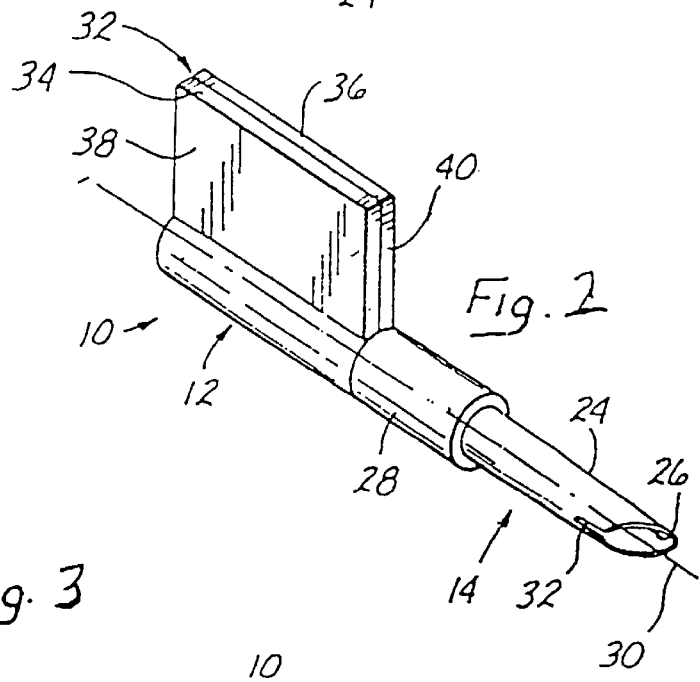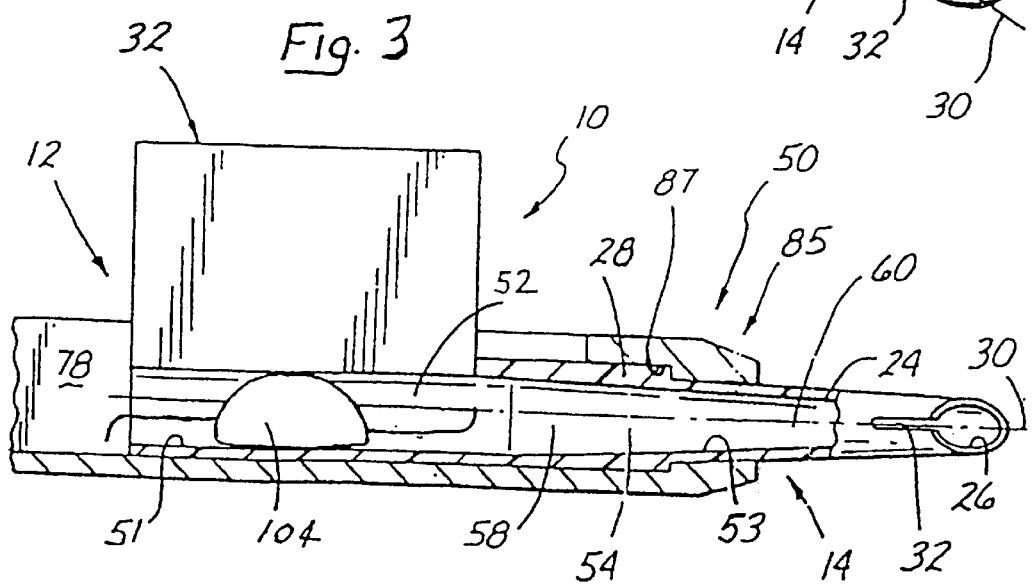

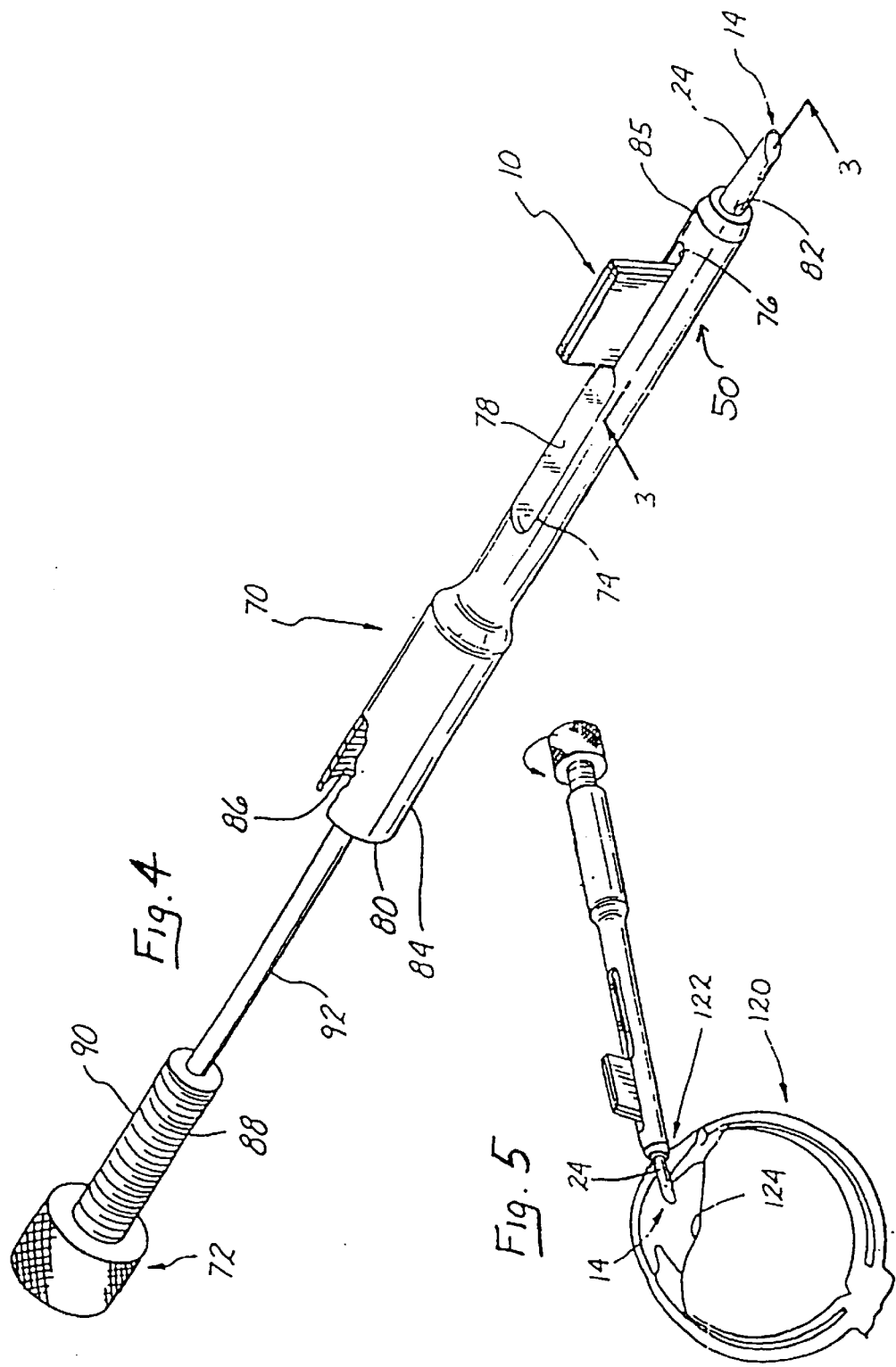

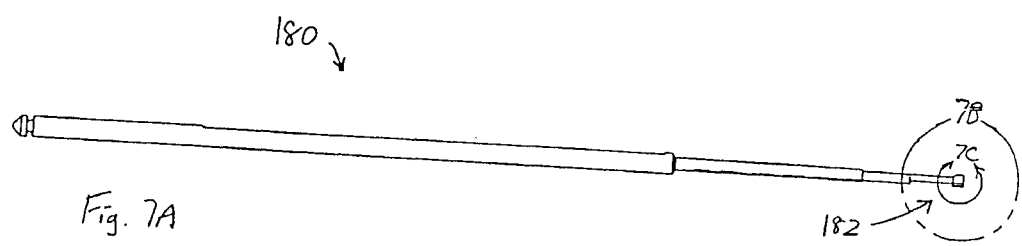
Fig. 7A
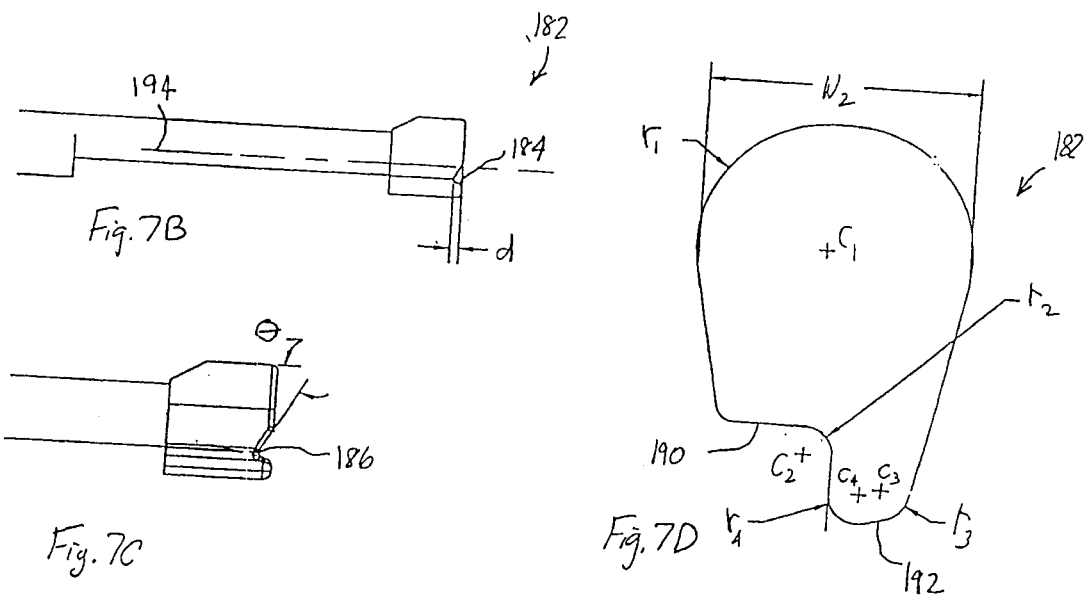
Fig. 7B
Fig. 7C
Fig. 7D

INTRAOCULAR LENS INSERTION APPARATUS

BACKGROUND OF THE INVENTION

The present invention relates to apparatus for inserting intraocular lenses (IOLs) into an eye. More particularly, the present invention relates to insertion apparatus having a hollow tube through which an acrylic IOL is pushed with a push rod into an eye.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

An intraocular lens (IOL) is implanted in the eye, for example, as a replacement for the natural crystalline lens after cataract surgery or to alter the optical properties of (provide vision correction to) an eye in which the natural lens remains. IOLs often include a disk-like optic, and preferably at least one flexible fixation member or haptic which extends radially outward from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible.

The optics may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through a small incision into the eye. A substantial number of instruments have been proposed to aid in inserting such a foldable lens in the eye. In a popular apparatus, the optic begins in the shape of a taco and is pushed through an insertion cartridge, progressively rolling into a tubular shape to fit through the incision. Such an exemplary insertion system is disclosed in Makker et al., U.S. Pat. No. 5,942,277, the contents of which are expressly incorporated by reference herein.

The two primary IOL materials are silicone and acrylic. Silicone IOLs are more pliable and can be folded into smaller tubes without unduly stressing the insertion cartridge, or requiring excessive push force which can violently expel the IOL from the cartridge. However, acrylic lenses are indicated for some patients and are inserted in much the same way as silicone IOLs, although using larger bore cartridges to mitigate the problems caused by the lower flexibility of the acrylic. Because the cartridge bore is larger, the incision is also necessarily larger.

In view of the foregoing, it would be beneficial in the art to provide an IOL insertion apparatus that enables acrylic IOLs to be inserted through smaller incisions.

SUMMARY OF THE INVENTION

The present invention provides new and enhanced apparatuses for implanting acrylic IOLs into the eye. The apparatuses enable acrylic IOLs to be inserted through smaller incisions than previously was possible. In general, the invention provides an insertion apparatus wherein a cartridge having a relatively small open distal mouth receives an acrylic IOL, and a modified push rod is used to urge the IOL through the cartridge.

In accordance with the first aspect of present invention, an insertion apparatus for intraocular lenses includes an intraocular lens having an optic and at least one fixation member, an insertion cartridge, and a push rod. The insertion cartridge has a proximal loading chamber sized to receive the intraocular lens in an unfolded configuration, and a distal injection tube having an open distal mouth sized to fit through an incision in the eye. The insertion cartridge further includes a lumen connecting the loading chamber and the open distal mouth that reduces in size therebetween to cause the intraocular lens to fold into a smaller size than its unfolded configuration when pushed through the lumen. The push rod has a distal tip for pushing the intraocular lens through the insertion cartridge from the loading chamber through the connecting lumen and out the open distal mouth. The push rod defines a longitudinal axis, and wherein the distal tip in transverse cross-section has a longitudinally extending runner on its lower surface and on one side thereof that creates an adjacent relief channel on the other side.

In accordance with a preferred aspect, the distal tip has a generally trapezoidal cross-section. Further, the distal tip in cross-section may have a cross-section perpendicular to the longitudinal axis that is non-symmetric across any plane that includes the longitudinal axis. In addition, the distal face of the distal tip they have a horizontal groove therein that creates a projection in the runner. The generally trapezoidal cross-section of the distal tip may have a rounded upper end that is larger than a lower end.

Desirably, the maximum cross-sectional dimension of the distal tip is slightly less than the inner diameter of the open distal mouth of the insertion cartridge. In one embodiment, the inner diameter of the open distal mouth of the insertion cartridge is less than about 2 mm.

In accordance with another aspect of the invention, and insertion apparatus for intraocular lenses comprises an intraocular lens having an optic and at least one fixation member, an insertion cartridge, and a push rod. The insertion cartridge is as described above, and the push rod has a distal tip for pushing the intraocular lens through the insertion cartridge from the loading chamber through the connecting lumen and out the open distal mouth. The push rod defines a longitudinal axis, and the distal tip of the push rod has at least one relief channel extending generally parallel to the longitudinal axis and on a lower side thereof. The relief channel is positioned to receive the fixation member of the intraocular lens as the distal tip contacts and pushes on the optic.

The distal tip may have a generally rounded trapezoidal cross-section, and a longitudinally extending runner on its lower surface and on one side thereof that creates the relief channel on the other side. In one embodiment, the distal face of the distal tip has a horizontal groove therein that creates a projection in the runner. Two relief channels may be provided on either side of the distal tip.

In accordance with a further aspect of the invention, an insertion apparatus for acrylic intraocular lenses comprises an intraocular lens having an acrylic optic and at least one fixation member. A polymer insertion cartridge having a proximal loading chamber is sized to receive the intraocular lens in an unfolded configuration. A distal injection tube on cartridge has an open distal mouth sized to fit through an incision in the eye. The insertion cartridge further includes a lumen connecting the loading chamber and the open distal mouth that reduces in size therebetween to less than about 2.0 mm at the open distal mouth to cause the intraocular lens to fold into a smaller size than its unfolded configuration when pushed through the lumen. At least a portion of the connecting lumen may have a lubrication enhancement incorporated into the polymer and concentrated near the surfaces of the cartridge.

Each and every feature described herein, and each and every combination of two or more of such features, is included within the scope of the present invention provided that the features included in such a combination are not mutually inconsistent.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

FIG. 1 is a front side view, in perspective, of an apparatus in accordance with the present invention with the load chamber in the open position.

FIG. 2 is a side view, in perspective, of the apparatus shown in FIG. 1 with the load chamber in the closed position.

FIG. 3 is a side view, partly in cross-section, taken generally along line 3—3 of FIG. 4.

FIG. 4 is a front side view, in perspective, of the apparatus shown in FIG. 2 loaded into a hand piece.

FIG. 5 is a somewhat schematic illustration showing the apparatus shown in FIG. 3, with the hand piece partially in cross-section, being used to insert an IOL into an eye.

FIG. 7A is an elevational view of a further exemplary push rod of the present invention.

FIGS. 7B–7D are various detailed views of the distal tip of the push rod of FIG. 7A.

DESCRIPTION OF THE PREFERRED EMBODIMENTS

Figure 6A:
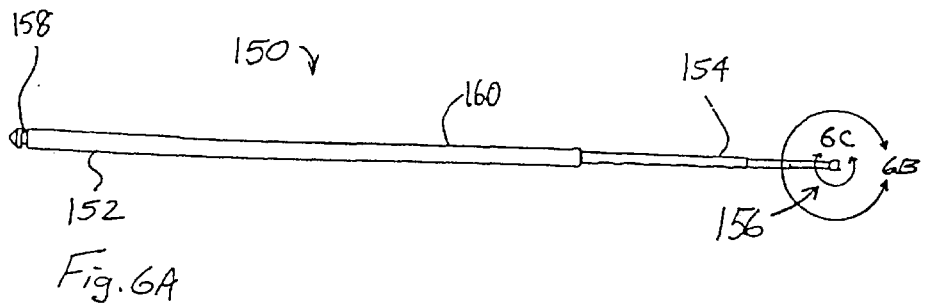
FIG. 6A is an elevational view of an exemplary push rod of the present invention.

FIGS. 1–3 illustrate an IOL inserter cartridge 10 of the present invention. The body of IOL cartridge 10 is an integrally formed, for example, molded, unit made primarily of polypropylene. A load chamber 12 includes a first member 16 and a second member 18 which are secured or joined together and are hingeably moveable relative to each other along line 21, which is parallel to the longitudinal axis 30 of cartridge 10.

And injection tube 14 includes a proximal end portion 22, a distal end portion 24 and an open distal mouth 26. A reinforcing collar 28 is coincidental with the proximal end portion 22 of injection tube 14. Open distal mouth 26 is beveled at an angle of about 45 degrees relative to the longitudinal axis 30 of the cartridge 10. Injection tube 14 may include a through slot 32 which extends from the open distal mouth 26 distally and terminates prior to the proximal end portion 22 of injection tube 14. Through slot 32 is elongated in a direction parallel to the longitudinal axis 30 of cartridge 10.

As shown in FIG. 1, cartridge 10 is in the opened position. In contrast, in FIG. 2, cartridge 10 is shown in the closed position. In the closed position, the load chamber 12 includes a top 32 which is a combination of top surfaces 34 and 36 of first wing 38 and second wing 40, respectively, of first member 16 and second member 18. First and second wings 38 and 40 are effective for a human user of cartridge 10 to hold and manipulate the cartridge 10 while using it, as described hereinafter.

Cartridge 10 is described in more detail with reference to FIG. 3, which shows the inserter in combination with a distal portion 50 of a hand piece. When used in combination with hand piece, the load chamber 12 of cartridge 10 is in the closed position. With the load chamber 12 in the closed position, and top 32 being the uppermost portion of the load chamber, open distal mouth 26 of injection tube 14 is beveled at an angle of 45 degrees relative to the longitudinal axis 30 of the cartridge 10 so that the open distal mouth is generally right facing (when the inserter is viewed from above). In addition, if present, through slot 32 intersects the open distal mouth 26 at the proximal most portion of the open distal mouth, as shown in FIGS. 1–3.

Still with reference to FIG. 3, the load chamber includes an interior wall 51 which defines a first lumen 52 that is elongated in a direction parallel to the longitudinal axis 30 of cartridge 10. Injection tube 14 includes a tapering interior wall 53 which defines a distally tapering second lumen 54. The average cross-sectional area of second lumen 54 transverse to the longitudinal axis 30 is smaller than or reduced relative to the average cross-sectional area of the first lumen 52.

The first lumen 52 is aligned with the second lumen 54 so that a folded IOL in the first lumen can be passed directly from the first lumen into the second lumen. The taper of proximal portion 58 of second lumen 54 is more severe than the slight taper which exists in the distal portion 60 of the second lumen. The more severe taper in the proximal portion 58 is effective to further fold the IOL as the IOL is passed into the second lumen 54. This further folding is advantageous because the further folded IOL can be inserted into the eye through a smaller incision.

Enhanced lubricity resulting from a component incorporated into the material of the cartridge 10 facilitates this further folding so that a reduced amount of force is required to further fold the IOL. Another benefit is that the degree of folding of the IOL may be increased so that ultimately the IOL can be inserted through an even smaller incision. The lubricity enhancing component also advantageously reduces the risk of tearing and/or otherwise damaging the IOL as the IOL is passed through the first lumen 52 and second lumen 54. A preferred lubricity enhancing component and application process is described below.

With reference to FIG. 4, cartridge 10 is shown in combination with hand piece 70 and push rod member 72. Hand piece 70 includes a relatively large, elongated first through opening 74 and a relatively small, elongated second through opening 76. Hand piece 70 includes a through bore 78 which extends from the proximal end 80 to the distal end 82 of the hand piece. The proximal end portion 84 of hand piece 70 includes threads 86 which are adapted to engage and mate with threads 88 of the proximal segment 90 of push rod member 72. Rod element 92 of push rod member 72 is adapted to pass through bore 78, first lumen 52, second lumen 54 and out of open distal mouth 26. Hand piece 70 and push rod member 72 are made of metal, such as titanium, surgical grade stainless steel or similar expedients.

Cartridge 10 is operated and functions as follows. When it is desired to load an IOL into cartridge 10, the inserter is placed, for example, manually placed, in a configuration as shown in FIG. 1. With load chamber 12 in the opened position, an IOL, such as is shown generally at 100, is placed, for example, using forceps, in between first and second members 16 and 18. This placement is such that the anterior face 102 of optic 104 faces upwardly, as shown in FIG. 1. The optic 104 is made of an acrylic polymeric material. Fillet haptics or fixation members 106 and 108 of IOL 100 are located as shown so that the fixation members are located generally parallel to, rather than transverse to, the longitudinal axis 30.

With IOL 100 placed as shown in FIG. 1, first and second members 16 and 18 are hingeably moved relative to each other, for example, by manually bringing first and second wings 38 and 40 together, to place the load chamber 12 in the closed position, as shown in FIG. 2. With load chamber 12 in the closed position, IOL 100 is in a folded state, that is optic 104 is folded. The relative movement of first and second members 16 and 18 to move the load chamber from the open position to the closed position is effective to fold the lens. The folded IOL 100 is now located in the first lumen 52 as seen in the cross-section of FIG. 5.

With the cartridge 10 configured as shown in FIG. 3 and folded IOL optic 104 located in first lumen 52, the cartridge 10 is placed in association with hand piece 70, as shown in FIG. 4. In this configuration, the distal end portion 24 of injection tube 14 extends distally beyond the distal end 82 of hand piece 70. As shown in FIG. 3, the distal portion 85 of hand piece 70 includes an inner wall 87 which is configured to receive reinforcing collar 28 in abutting relation.

Referring now to FIG. 5, the IOL 100 is to be placed in eye 120 into an area formerly occupied by the natural lens of the eye. FIG. 5 shows the sclera 122 having an incision through which the distal end portion 24 of injection tube 14 is passed. Alternately, the incision can be made through the cornea. Distal end portion 24 has a sufficiently small cross-section to pass into the eye 122 through a 3.0 mm incision in the sclera 122.

With cartridge 10 position within the hand piece 70, the push rod member 72 is placed into the through bore 78 of the hand piece starting at the proximal end 80. As threads 88 come in contact with and engage threads 86, the push rod member 72 is rotated, as shown in FIG. 5, so as to thread the push rod member onto the proximal end portion 84 of hand piece 70. By gradually moving push rod element 92 through bore 78 of hand piece 70, the folded IOL 100 is urged to move from first lumen 52 into second lumen 56, through open distal mouth 26 and into the eye.

The injection tube 14 is manipulated within eye 122 until it is positioned so that IOL 100 can be properly positioned in eye 122, that is in the anterior chamber, the posterior chamber, the capsular bag 124 or in the sulcus, after being released. Thus, the surgeon is able to controllably position the distal end portion 24 of injection tube 14, with IOL 100 in the first lumen 52 of load chamber 12. Once distal end portion 24 is so positioned, the rod element 92 is urged distally, by rotating (threading) push rod member 72 onto hand piece 70, to pass the IOL 100 into and through the second lumen 54, through the open distal mouth 26 of injection tube 14 and into the eye 120.

The anterior face 102 of IOL 100 faces generally forwardly in the eye 120 as the IOL is released from the cartridge 10. In other words, the IOL 100 passes through first lumen 52, second lumen 54 and open distal mouth 26 and into eye 120 without flipping or otherwise becoming mispositioned. Only a relatively small amount of, if any, post-insertion re-positioning is needed to properly position IOL 100 in eye 120.

After the IOL 100 has been inserted into the eye, the rod element 92 is moved proximally into the injection tube 14 and the distal end portion 24 of the injection tube is removed from the eye. If needed, the IOL 100 can be repositioned in the eye by a small, bent needle or similar tool inserted into the same incision.

Once the IOL 100 is properly positioned in eye 120 and cartridge 10 is withdrawn from the eye, the incision in the sclera may be mended, for example, using conventional techniques. After use, the cartridge 10 is preferably disposed of. Hand piece 70 and push rod member 72 can be reused, after sterilization/disinfection.

The present invention concerns the insertion of acrylic intraocular lenses into the eye. Such lenses typically have an acrylic optic and haptics or fixation members that are polymethyl methacrylate (PMMA) or other suitable material. Three-piece (i.e., an optic and two haptics) IOLs with acrylic optics have previously been limited to insertion through incisions of greater than 3.2 mm because of the difficulties associated with folding such optics into the small size necessary to pass it through smaller incisions. That is, because acrylic optics are relatively less flexible or pliable than, for example, silicone optics, a greater force is necessary to fold them into a tube. Subsequently, the acrylic optic exerts a relatively high unfolding force on the injector cartridge. Cartridges have thus been used that are relatively larger than those used for silicone optics to limit the degree to which the acrylic optic is folded, and withstand the outward force exerted by the optic. Furthermore, an acrylic IOL is more difficult to push down any particular tube relative to a silicone IOL, and thus a greater push force is needed. Unfortunately, high push forces can result in the IOL being distorted or not delivered into the patient's eye.

The present invention therefore solves a long-standing problem that has created a disadvantage in the use of acrylic IOLs; that of requiring a relatively larger incision in the eye. The solution arises from a combination of factors, each of which may contribute relatively more less than the others.

First of all, of course, a smaller injection tube 14 is used to insert acrylic IOLs. The injection tube 14 desirably has an open distal mouth 26 (see FIG. 1) having an inner diameter of no more than 2.0 mm, preferably no more than 1.8 mm (0.073 inches). Previously, such small injection tubes, which are made of a polymer and injection molded, were unable to reliably withstand the outward forces exerted by acrylic IOLs. One solution would be to increase the wall thickness of the tube, but this also increases the outer diameter which necessitates a larger incision, thus limiting any benefit from a smaller tube. In the present invention, the maximum wall thickness of the injection tube 14 is desirably about 0.15 mm (0.006 inches) and is manufactured so as to be highly uniform. The minimum wall thickness of the injection tube 14 is desirably about 0.11 mm (0.0045 inches) Therefore, the outer diameter of the open distal mouth 26 is less than about 2.7 mm, desirably less than about 2.2 mm, which enables insertion through incisions of less than about 2.8 mm.

The prior art has not recognized the need for a more accurate manufacturing process to insure a uniform wall thickness. In any such injection molding process, or in any manufacturing process for that matter, there is always a trade-off between increased tolerances and/or quality-control and economics. Up until now there has not been a recognized justification for increasing the uniformity of the wall thickness of such injection tubes. As one of skill the art will understand, there are various ways to insure the wall thickness of the injection tube 14 is uniform, and all such manufacturing process improvements are incorporated by the present invention. For example, the tolerances on the molds could be tightened.

A second contribute factor enabling acrylic IOLs to be inserted to smaller incisions involves designing the rod element 92 of push rod member 72 described above with respect to FIGS. 1–5 to effectively and safely push an acrylic IOL through an IOL insertion cartridge of the present invention. FIGS. 6–7 illustrates two different embodiments of a push rod of the present invention.

Finally, as mentioned above, the cartridge 10, or at least the inner lumens, may be treated so as to have enhanced lubricity. Makker et al. (U.S. Pat. No. 6,083,230) describe various methods for making the inner bore of a polypropylene IOL insertion cartridge lubricious. The methods include subjecting a polypropylene cartridge having a lubricity enhancing component therein to elevated temperatures so as to "bloom" the polymer. Additionally, the inner bore of the cartridge may be exposed to a plasma to concentrate the lubricity enhancing component near the inner surface thereof. Finally, a surface coating of another lubricity enhancing component can be added. All these methods may be used in conjunction with the IOL insertion cartridge of the present invention, and disclosure in Makker et al. is incorporated by reference.

In a particular preferred embodiment, the present cartridge 10 is made of a polymeric material such as polypropylene that has a lubricity enhancing component evenly distributed throughout. The lubricity enhancing component is desirably an oleophilic component such as glycerol monostearate or a hydrophilic compound such as polyvinyl pyrrolidone. The cartridge 10 is subjected to an elevated temperature for a time effective to cause the lubricity enhancing component to migrate toward the surfaces thereof. This technique is known as "blooming."

With respect to FIG. 6A, a push rod element 150 includes a proximal shaft 152, an intermediate shaft 154 that narrows in steps, and a distal tip 156. The push rod element 150 further includes an annular groove 158 on its proximal end that is adapted to receive a collar or other such cooperating member on a threaded handle (not shown). With reference back to FIG. 4, the push rod member 72 shown is somewhat simplistic, because the push rod element 92 is normally journaled so as to rotatably with respect to the threads 90. In this manner, the push rod element 92 can be displaced axially without rotation (and without imparting any rotation to the IOL). To this end, the push rod element 150 includes a flat 160 on one side that cooperates with structure on the inside of the hand piece to prevent rotation thereof.

Figure 6B:
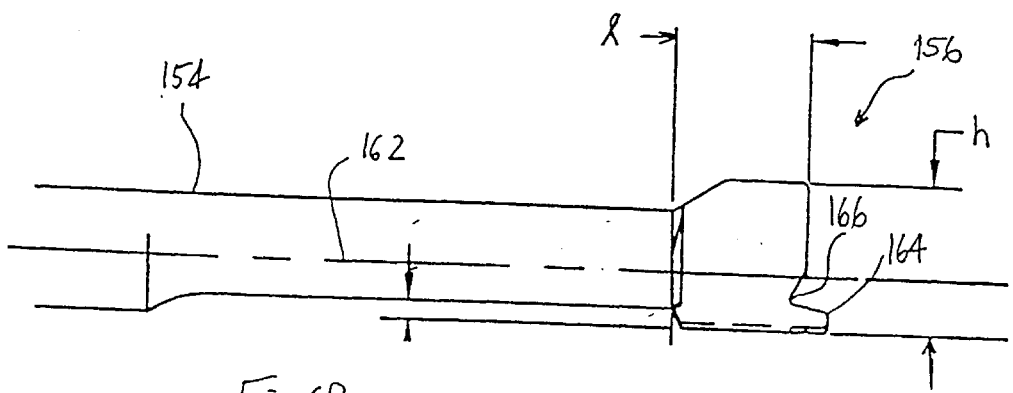
FIGS. 6B–6D are various detailed views of the distal tip of the push rod of FIG. 6A.
Figure 6C:
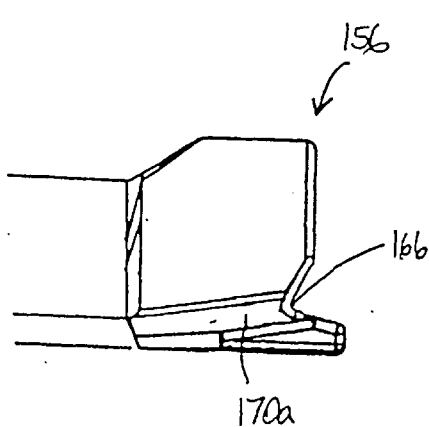
Figure 6D:
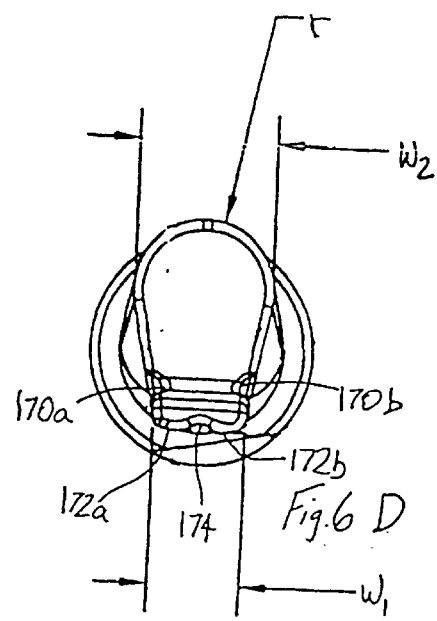

FIGS. 6B–6D illustrate the distal tip 156 and various dimensions thereof. The longitudinal axis 162 of the entire push rod element 150 is shown in FIG. 6B, and it can be seen that the distal tip 156 is off center in the vertical direction. In an exemplary embodiment, the entire height h of the distal tip 156 is about 1.8 mm (0.07 inches), and approximately 60 percent of the height is above the centerline 162. Furthermore, the distal tip 156 is taller than the adjacent intermediate shaft 154. It will be understood that the distal tip 156 is oriented in the position it would be as it enters the cartridge 10 with the first and second wings 38 and 40 oriented upward (see FIG. 3). The axial dimension 1 of the distal tip 156 is desirably about 1.6 mm (0.065 inches).

With reference to FIG. 6B, the distal tip includes a lower chin 164 that projects distally from the remainder of the tip by approximately 0.28 mm (0.011 inches). A distally facing groove 166 exists adjacent the chin 164 and receives a trailing fixation member or haptic of the IOL after the entire IOL has been ejected from the cartridge. That is, a trailing haptic may require some further manipulation within the eye and the chin 164 and groove 166 permit the surgeon to capture the haptic and move it around in the eye.

FIG. 6C illustrates various curvilinear contours of the distal tip 156 that are not illustrated in FIG. 6B because there are no sharp transitions. Most importantly, and as also seen from the end in FIG. 6D, the distal tip 156 possesses a pair of relief channels 170a, 170b on either side thereof. These relief channels 170a, 170b extend substantially the entire axial length 1 of the distal tip 156 and are slightly downwardly angled from the groove 166 in a proximal direction. The relief channels 170 are sized to receive a trailing haptic of the IOL during the process of urging the IOL through the cartridge.

That is, the trailing haptic fits within one of the relief channels 170 to prevent it from becoming damaged by compression between the distal tip 156 and the cartridge bore.

As seen from the end in FIG. 6D, the distal tip 156 has a tapered cross-section beginning in a narrow width w1 at the bottom and becoming gradually larger to a width w2 at the top. In an exemplary embodiment, w1 is about 0.76 mm (0.031 inches), while w2 is about 1.16 mm (0.046 inches). The upper surface of the distal tip is curved by a radius r of about 0.56 mm (0.022 inches). The overall rounded shape of the distal tip 156 helps prevent damage to the acrylic optic. The overall cross-sectional shape of the distal tip 156 is a rounded trapezoid. The bottom surface of the distal tip 156 includes a pair of longitudinal runners 172a, 172b separated by a groove 174. The runners 172 help center the distal tip 156 within the cartridge bore as it urges the IOL therethrough.

FIG. 7A illustrates an alternative push rod element 180 that is in most aspects similar to the push rod element 150 described above, except for having a modified distal tip 182. The distal tip 182 is shown in the several views of FIGS. 7B–7D.

The axial lengths and height dimensions of the distal tip 182 are substantially the same as for the distal tip 156 described above. The distal tip 182 also includes a lower lip 184 but it does not extend beyond the remainder of the tip, as seen in FIGS. 7B and 7C. A groove 186 is once again provided to capture the trailing haptic once the IOL is released from the cartridge. The groove 186 desirably has a depth d of about 2.0 mm (0.08 inches). The lower wall of the groove 156 forms the upper wall of the chin 184, while the upper wall of the groove is formed at an angle theta of about 60 degrees with the vertical.

With reference now to FIG. 7D, the distal tip 182 has the rounded tapered configuration as to the distal tip 156 described previously. However, instead of having two relief channels either side, the distal tip 182 has a single enlarged relief channels 190 only on one side and open to the bottom surface of the tip. A single longitudinal runner 192 is thus created adjacent to the relief channel 190. The longitudinal runner 194 helps center the distal tip 182 within the cartridge. It should be noted that the chin 184 is formed entirely on the runner 194. The relief channel 190 is the again provided to receive a trailing haptic of the IOL. The largest width w2 and radius r of the distal tip 182 are similar to those dimensions in the tip 156 described above. Several radii and corresponding centers are illustrated to help described the asymmetric cross-section perpendicular to the longitudinal axis 194, and curvatures of the distal tip 182. Once again, the overall shape is generally a rounded trapezoid. In contrast to prior push rod tips, the distal tip 182 is asymmetric about any plane that includes the longitudinal axis 194 of the push rod element 180. This asymmetry is heretofore unknown and provides certain advantages, such as enabling the distal tip 182 to successfully push acrylic IOLs through the cartridge of the present invention. Also, the asymmetric relief channel 190 effectively receives the trailing haptic of the IOL and prevents damage thereto.

While the present invention has been described with respect to various specific examples and embodiments, it is to be understood that the invention is not limited thereto and that it can be variously practiced within the scope of the following claims.

What is claimed is:

1. An insertion apparatus for inserting an intraocular lens having an optic and at least one fixation member in a patient's eye, comprising:
    an insertion cartridge having a proximal loading chamber sized to receive the intraocular lens in an unfolded configuration, and a distal injection tube having an open distal mouth sized to fit through an incision in the eye, the insertion cartridge further including a lumen connecting the loading chamber and the open distal mouth that reduces in size therebetween to cause the intraocular lens to fold into a smaller size than its unfolded configuration when pushed through the lumen; and
    a push rod having a distal tip for pushing the intraocular lens through the insertion cartridge from the loading chamber through the connecting lumen and out the open distal mouth, the push rod defining a longitudinal axis and wherein the distal tip in transverse cross-section has a longitudinally extending runner on its lower surface and on one side thereof that creates an adjacent relief channel on the other side.

2. The insertion apparatus of claim 1, wherein the distal tip has a generally trapezoidal cross-section.

3. The insertion apparatus of claim 2, the distal tip of the push rod has a cross-section perpendicular to the longitudinal axis that is non-symmetric across any plane that includes the longitudinal axis.

4. The insertion apparatus of claim 2, wherein the distal tip has a rounded upper end that is larger than a lower end.

5. The insertion apparatus of claim 1, wherein the distal face of the distal tip has a horizontal groove therein that creates a projection in the runner.

6. The insertion apparatus of claim 1, wherein the maximum cross-sectional dimension of the distal tip is slightly less than the inner diameter of the open distal mouth of the insertion cartridge.

7. The insertion apparatus of claim 6, wherein the inner diameter of the open distal mouth of the insertion cartridge is less than about 2 mm.

8. The insertion apparatus of claim 1, further including:
    a hand piece having a through bore extending from a proximal end to a distal end thereof for receiving and aligning the push rod with the cartridge lumen.

9. The insertion apparatus of claim 8, wherein the hand piece through bore includes threads which are adapted to engage and mate with threads on the push rod for controlled movement thereof.

10. The insertion apparatus of claim 1, wherein the insertion cartridge is made of a polymer with a lubricity enhancing component therein, and wherein the lubricity enhancing component is concentrated near the surfaces of the cartridge by a blooming process involving elevating the temperature of the cartridge for a period of time.

11. The insertion apparatus of claim 10, wherein the lubricity enhancing component is an oleophilic component.

12. An insertion apparatus for inserting an intraocular lens having an optic and at least one fixation member in a patient's eye, comprising:
    an insertion cartridge having a proximal loading chamber sized to receive the intraocular lens in an unfolded configuration, and a distal injection tube having an open distal mouth sized to fit through an incision in the eye, the insertion cartridge further including a lumen connecting the loading chamber and the open distal mouth that reduces in size therebetween to cause the intraocular lens to fold into a smaller size than its unfolded configuration when pushed through the lumen; and
    a push rod having a distal tip for pushing the intraocular lens through the insertion cartridge from the loading chamber through the connecting lumen and out the open distal mouth, the push rod defining a longitudinal axis and the distal tip of the push rod having at least one relief channel extending generally parallel to the longitudinal axis and on a lower side thereof, the relief channel being positioned to receive the fixation member of the intraocular lens as the distal tip contacts and pushes on the optic.

13. The insertion apparatus of claim 12, wherein the distal tip has a generally rounded trapezoidal cross-section.

14. The insertion apparatus of claim 12, wherein the distal tip in cross-section has a longitudinally extending runner on its lower surface and on one side thereof that creates the relief channel on the other side.

15. The insertion apparatus of claim 14, wherein the distal face of the distal tip has a horizontal groove therein that creates a projection in the runner.

16. The insertion apparatus of claim 14, further including:
    a hand piece having a through bore extending from a proximal end to a distal end thereof for receiving and aligning the push rod with the cartridge lumen.

17. The insertion apparatus of claim 16, wherein the hand piece through bore includes threads which are adapted to engage and mate with threads on the push rod for controlled movement thereof.

18. The insertion apparatus of claim 12, wherein two relief channels are provided on either lower side of the distal tip.

19. The insertion apparatus of claim 18, wherein the distal face of the distal tip has a horizontal groove and a chin below the groove that projects distally from the distal face.

20. The insertion apparatus of claim 12, wherein the maximum cross-sectional dimension of the distal tip is slightly less than the inner diameter of the open distal mouth of the insertion cartridge.

21. The insertion apparatus of claim 20, wherein the inner diameter of the open distal mouth of the insertion cartridge is less than about 2 mm.

22. The insertion apparatus of claim 10, wherein the insertion cartridge is made of a polymer with a lubricity enhancing component therein, and wherein the lubricity enhancing component is concentrated near the surfaces of the cartridge by a blooming process involving elevating the temperature of the cartridge for a period of time.

23. The insertion apparatus of claim 22, wherein the lubricity enhancing component is an oleophilic component.

* * * * *